US006566095B1

(12) United States Patent
Markham et al.

(10) Patent No.: US 6,566,095 B1
(45) Date of Patent: May 20, 2003

(54) COMPOSITIONS AND METHODS FOR PREVENTING TRANSEPITHELIAL TRANSMISSION OF HIV

(75) Inventors: Richard B. Markham, Columbia, MD (US); Kristen V. Khanna, Columbia, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/599,555

(22) Filed: Jun. 23, 2000

Related U.S. Application Data
(60) Provisional application No. 60/140,698, filed on Jun. 24, 1999.

(51) Int. Cl.[7] ............................ C12P 21/06; A61K 39/42
(52) U.S. Cl. ................. 435/69.1; 424/159.1; 424/160.1
(58) Field of Search ...................... 435/69.1; 424/159.1, 424/160.1

(56) References Cited

U.S. PATENT DOCUMENTS

| | | | |
|---|---|---|---|
| 5,324,510 A | 6/1994 | Wegner et al. ............. 424/85.8 |
| 5,475,091 A | 12/1995 | Springer et al. ......... 530/388.22 |
| 5,525,487 A | 6/1996 | Gallatin et al. ............ 435/68.1 |
| 5,532,127 A | 7/1996 | Gallatin et al. ................. 435/6 |
| 5,651,970 A | 7/1997 | Allen ...................... 424/154.1 |
| 5,663,293 A | 9/1997 | Gallatin et al. ............. 530/324 |
| 5,674,982 A | 10/1997 | Greve et al. ............ 530/388.22 |
| 5,733,540 A | 3/1998 | Lee .......................... 424/93.1 |
| 5,891,841 A | 4/1999 | DeFougerolles et al. ........ 514/2 |

FOREIGN PATENT DOCUMENTS

| | | |
|---|---|---|
| EP | 0 745 852 A1 | 12/1996 |
| WO | WO 90/13281 | 11/1990 |
| WO | WO 90/13316 | 11/1990 |
| WO | WO 91/16927 | 11/1991 |
| WO | WO 91/16928 | 11/1991 |
| WO | WO 91/18010 | 11/1991 |

OTHER PUBLICATIONS

Notification of Transmittal of the International Search Report or the Declaration dated Nov. 17, 2000.
M. O. Borghi, et al.—2000. "Interaction between chronically HIV–infected promonocytic cells and human umbilical vein endothelial cells: role of proinflammatory cytokines and chemokines in viral expression modulation." Clin Exp Immunol 120:93.
R. G. Chirivi, et al.—1999. "Human immunodeficiency virus–1 (HIV–1)–Tat protein promotes migration of acquired immunodeficiency syndrome–related lymphoma cells and enhances their adhesion to endothelial cells." Blood 94:1747.
S. Fais, et al.—1995. "Unidirectional budding of HIV–1 at the site of cell–to–cell contact is associated with co-polarization of intercellular adhesion molecules and HIV–1 viral matrix protein." Aids 9:329.

(List continued on next page.)

Primary Examiner—Hankyel T. Park
(74) Attorney, Agent, or Firm—Whitham, Curtis & Christofferson, P.C.

(57) ABSTRACT

Methods, compositions and articles for blocking transepithelial transmission of HIV with ICAM-1 angonist/antagonists are provided. The ICAM-1 agonist/antagonists block viral transmission at the site of exposure to the virus. Blocking viral transmission does not require blocking the binding of ICAM-1 to LFA-1. The ICAM-1 agonist/antagonists may be applied to mucosal surfaces, on or in contraceptive devices or in oral solutions such as breast milk supplements and infant formula.

33 Claims, 5 Drawing Sheets

OTHER PUBLICATIONS

Figure 1A:
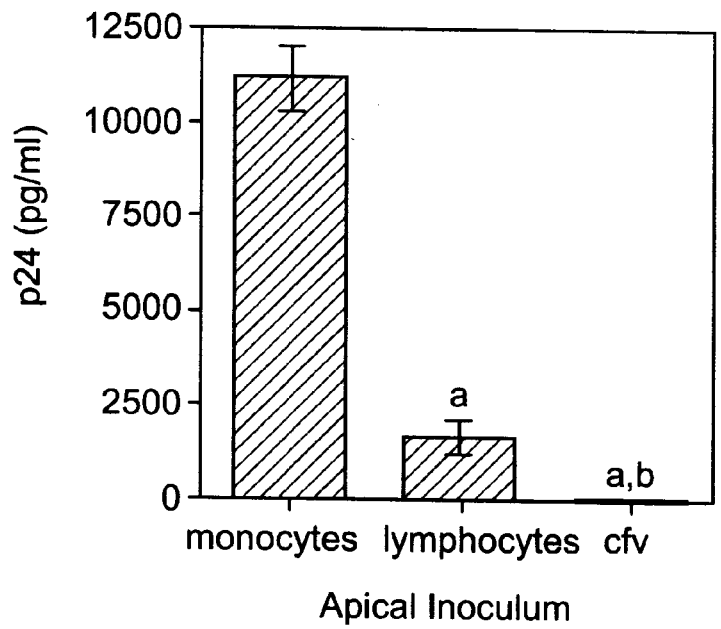

S. Fais, et al.—1996. "Human immunodeficiency virus type 1 induces cellular polarization, intercellular adhesion molecule–1 redistribution, and multinucleated giant cell generation in human primary monocytes but not in monocyte-derived macrophages" (published erratum appears in Lab Invest 1997 Sep; 77(3):194). Lab Invest 75:783.

J.F. Fortin, et al.—1997. "Host–derived ICAM–1 glycoproteins incorporated on human immunodeficiency virus type 1 are biologically active and enhance viral infectivity." J. Virol 71:3588.

J.F. Fortin, et al.—1998. "T cells expressing activated LFA–1 are more susceptible to infection with human immunodeficiency virus type 1 particles bearing host–encoded ICAM–1." J Virol. 72:2105.

J. F. Fortin, et al.—1999. Role of the leukocyte function antigen–1 conformational state in the process of human immunodeficiency virus type 1–mediated syncytium formation and virus infection. Virology 257:228.

J. F. Fortin, et al.—2000. "Interaction between virion–bound host intercellular adhesion molecule–1 and the high–affinity state of lymphocyte function–associated antigen–1 on target cells renders R5 and X4 isolates of human immunodeficiency virus type 1 more refractory to neutralization." Virology 268:493.

E. J. Gaddi, et al.—1999. "Soluble intercellular adhesion molecule–1 (ICAM–1) levels in HIV infected children." Medicina 59:351.

J. E. Hildreth, et al.—1999. "Production and characterization of monoclonal antibodies against pigtailed macaque (*Macaca nemestrina*) cell adhesion molecules." Hybridoma 18:437.

Z. Liao, et al.—2000. "Increased infectivity of HIV type 1 particles bound to cell surface and solid–phase ICAM–1 and VCAM–1 through acquired adhesion molecules LFA–1 and VLA–4." AIDS Res. Hum. Retroviruses 16:355.

H. S. Nottet—1999. "Interactions between macrophages and brain microvascular endothelial cells: role in pathogenesis of HIV–1 infection and blood—brain barrier function." J Neurovirol 5:659.

J. S. Paquette, et al.—1998. "Level of ICAM–1 surface expression on virus producer cells influences both the amount of virion–bound host ICAM–1 and human immunodeficiency virus type 1 infectivity." J. Virol 72:9329.

C. D. Rizzuto, et al.—1997. "Contribution of virion ICAM–1 to human immunodeficiency virus infectivity and sensitivity to neutralization." J Virol 71:4847.

R. D. Rossen, et al.—1989. "HIV–1 stimulated expression of CD11/CD18 integrins and ICAM–1: a possible mechanism for extravascular dissemination of HIV–1–infected cells." Trans Assoc Am Physicians 102:117.

O. V. Scheglovitova, et al.—1995. "Antibody to ICAM–1 mediates enhancement of HIV–1 infection of human endothelial cells." Arch Virol 140:951.

H. I. Stoiber, et al.—1997. "Inhibition of HIV–1 infection in vitro by monoclonal antibodies to the complement receptor type 3 (CR3): an accessory role for CR3 during virus entry?" Mol Immunol 34:855.

Y. Tsunetsuga–Yokota, et al.—1997. "Efficient virus transmission from dendritic cells to CD4+ T cells in response to antigen depends on close contact through adhesion molecules." Virology 239:259.

Khanna, K.V., et al., "Vaginal transmission of cell–associated HIV–1 in the mouse is blocked by a topical, membrane–modifying agent", The Journal of Clinical Investigation, vol. 109, No. 2, pp. 205–211, (Jan. 2002).

Hioe, C.E., et al., "Role of Cellular Adhesion Molecules in HIV Type I Infection and Their Impact on Virus Neutralization", Aids Research and Human Retroviruses, vol. 14, Suppl. 3, pp. S247–S254, (1998).

Hioe, C.E., et al., "Enhanced HIV Type I Neutralization by Human Anti–Glycoprotein 120 Monoclonal Antibodies in the Presence of Monoclonal Antibodies to Lymphocyte Function–Associated Molecule 1", Aids Research and Human Retroviruses, vol. 15, No.6, pp. 523–531 (1999).

Hansen, J–E.S., et al., "Involvement of Lymphocyte Function–Associated Antigen–1(LFA–1) in HIV Infection: Inhibition by Monoclonal Antibody", Scand J Infect Dis, vol. 23, No. 1, pp. 31–36 (1991).

Paquette, J–S., et al., "Level of ICAM–1 Surface Expression on Virus Producer Cells Influences both the Amount of Virion–Bound Host ICAM–1 and Human Immunodeficiency Virus Type 1 Infectivity", Journal of Virology, vol. 71, No. 11, pp. 9329–9336 (1998).

Fortin, J–F., et al., "T Cells Expressing Activated LFA–1 Are More Suspectible to Infection with Human Immunodeficiency Virus Type 1 Particles Bearing Host–Encoded ICAM–1", Journal of Virology, vol. 71, No. 3, pp. 2105–2112 (1998).

Rizzuto, C.D., et al., "Contribution of Virion ICAM–1 to Human Immunodeficiency Virus Infectivity and Sensitivity to Neutralization", Journal of Virology, vol. 71, No. 6, pp. 4847–4851 (1997).

Fortin, J–F., et al., "Host–Derived ICAM–1 Glycoproteins Incorporated on Human Immunodeficiency Virus Type 1 are Biologically Active and Enhance Viral Infectivity", Journal of Virology, vol. 71, No. 5, pp. 3588–3596 (1997).

Basilar p24

| Inoculum | 1 x 10$^6$ | 5 x 10$^5$ | 1 x 10$^5$ | 5 x 10$^4$ | 1 x 10$^4$ | 5 x 10$^3$ | 1 x 10$^3$ | 5 x 10$^2$ |
|---|---|---|---|---|---|---|---|---|
| Exp #1 | +++ | +++ | +++ | ++ | ++ | + | + | - |
| Exp #2 | +++ | +++ | ++ | ++ | ++ | + | - | - |

COMPOSITIONS AND METHODS FOR PREVENTING TRANSEPITHELIAL TRANSMISSION OF HIV

This application claims priority to U.S. Provisional Patent Application No. 60/140,698 filed on Jun. 24, 1999 which is hereby incorporated by reference in its entirety.

The United States Government has certain rights in this invention pursuant to Grant Numbers DA 09717, DA 09973, DA 05972 and AI 07417, funded by the NIDA and NIAID respectively.

FIELD OF THE INVENTION

The field of this invention relates to methods, compositions and articles of manufacture for preventing transmission of the human immunodeficiency virus ("HIV"). In a particularly preferred embodiment, the invention relates to ICAM-1 agonist/antagonists and their use to prevent the transmission of HIV across mucosal surfaces.

REFERENCES

Several publications are referenced herein. Full citations for these publications are provided below. The disclosures of these publications are hereby incorporated herein by reference in their entirety, unless otherwise noted.

BACKGROUND OF THE INVENTION

Understanding the mechanisms of viral transmission is critical for preventing the spread of HIV, the causative agent of Acquired Immune Deficiency Syndrome (AIDS). Limiting the AIDS pandemic worldwide depends, in large part, on the ability to prevent fiurther transmission and spread of HIV.

A critical feature of sexual transmission of HIV-1 is that the vaginal or mucosal surface that is initially exposed to this virus is covered with epithelial cells, which are not among the cells that are usually associated with HIV-1 infection. To cross this barrier, virus must (1) directly transverse or infect epithelial cells, (2) be associated with cells that can migrate between epithelial cells, or (3) come into contact with injectable host cells that extend between epithelial cells. Experimental evidence exists to support all of these possibilities. Previous studies suggest that epithelial cells can be productively infected, but that transmission to and from these cells requires direct interaction with infected or injectable cells.

Physical contact between latent HIV-infected leukocytes, CD4 leukocytes and epithelial cells from unrelated individuals triggers rapid assembly and release of HIV-1 into the enclosed space between donor and acceptor cells. During this process, monocytes form microvilli that intimately associate with epithelial membrane. Virions sequestered in these sites are then internalized in the epithelial cells within phagocytic endosomes. These observations, supported by abundant additional studies, demonstrate that cell-cell interaction is critical to the efficient transmission of HIV-1 to and from epithelial cells.

ICAM-1 is a single-chain glycoprotein adhesion molecule constitutively expressed on resting endothelial cells, resting monocytes, resting epithelial cells as well as activated T-cells. ICAM-1 expression is induced by a variety of cytokines including IFN-γ, TNFα, and IL-1. The CD18 family of cellular adhesion molecules mediate interactions between cells of the immune and inflammatory system. LFA-1, also known as Lymphocyte Function-Associated Antigen-1 or CD11a/CD18, recognizes and binds to ICAM-1, ICAM-2 and ICAM-3 on the endothelium. The heterodimeric structure of LFA-1 consists of an alpha and a beta chain. As a member of the integrin family, LFA-1 plays a role in many cellular processes such as migration, antigen presentation, and cell proliferation. For example, LFA-1 mediates the binding of leukocytes to endothelial cells permitting the migration of leukocytes from the bloodstream into the tissue. ICAM-1 is the primary ligand for LFA-1. ICAM-1 is anchored to the endothelium by a transmembrane domain, has a short cytoplasmic tail, contains five extracellular immunoglobulin-like domains, and is expressed on HIV-infected monocytes and epithelial cells.

U.S. Pat. No. 5,891,841 ("the '841 patent") is directed to methods of using intracellular adhesion molecules (ICAM-3) to suppress migration of HIV-1 infected cells from the circulatory system. According to the '841 patent, induction of ICAM-1 on epithelial cells, endothelial cells, and fibroblasts mediates LFA-1 dependent adhesion of lymphocytes (col. 12, lines 48–50). LFA-1 and ICAM-1 are receptors for one another and are referred to in the '841 patent as "receptor" and "ligand" respectively. Id. In particular, the '841 patent implicates the interaction between ICAM-1 and LFA-1 in the formation of HIV-induced syncytium formation. According to the '841 patent, LFA-1 has the greatest affinity for ICAM-1 in comparison to ICAM-2 and ICAM-3 (col. 14, lines 9–16).

U.S. Pat. No. 5,674,982 ("the '982 patent") refers to the use of anti-ICAM-1 antibodies to reduce the infectivity of rhinovirus by interfering with the interaction between LFA-1 and ICAM-1. PCT Application WO 90/13316 A1 refers to a method of suppressing the migration of HIV-1 infected cells from the circulatory system by impairing the ability of the HIV-infected leukocyte to bind to ICAM-1 or a member of the CD11/CD18 family of receptor molecules.

The role of such adhesion molecules in the transepithelial transmission of cell-associated or cell-free virus has not been addressed. Previous methods and compositions are directed to blocking the interaction of ICAM-1 and LFA-1 to prevent migration of viruses from the circulatory system at sites distant from the site of initial exposure. The role of ICAM-1, independent of its interaction with LFA-1, in viral transmission at the site of exposure to HIV or at the point of viral entry into the body, has not been addressed.

What is needed are methods and composition for blocking transepithelial transmission of HIV at the site of exposure to the virus.

SUMMARY OF THE INVENTION

This invention provides new methods, compositions, and articles of manufacture for preventing the transepithelial, transmission of HIV to an animal. Prior art methods involving ICAM-1 are directed to interfering with the ICAM-1/LFA-1 binding and preventing migration of virus from the circulatory system, across endothelial cells, into body tissue. The present invention is directed to blocking transepithelial transmission of HIV at the site of exposure to the virus, and prevents HIV infection rather than treating infection after the fact.

In a preferred embodiment, the invention provides a method of blocking transepithelial transmission of HIV at the site of exposure to the virus using an ICAM-1 agonist/antagonist. In another preferred embodiment, the blocking of viral transmission does not require blocking the binding of ICAM-1 to LFA-1. In further preferred embodiment, the invention provides a method of blocking transepithelial transmission of HIV across mucosal surfaces, e.g., genital, vaginal, rectal, oral, gastrointestinal, using a composition or article of manufacture containing an ICAM-1 agonist/antagonist. Also provided are methods of using genetically-modified bacteria capable of producing an ICAM-1 agonist/antagonist for inoculating a mucosal surface.

In another preferred embodiment, the present invention provides a pharmaceutical composition for blocking transepithelial transmission of HIV comprising an ICAM-1 agonist/antagonist and a pharmaceutically acceptable carrier. In yet another preferred embodiment, the invention provides an article of manufacture comprising an ICAM-1 agonist/antagonist and a substrate. The preferred substrates include cervical rings, condoms and intrauterine devices.

Additional embodiments and advantages of the present invention will be set forth in part in the description that follows, and in part will be obvious from the description, or may be learned through the practice of the invention. The objects and advantages of the invention will be attained by means of the instnumentalities and combinations particularly pointed out in the appended claims.

BRIEF DESCRIPTION OF THE DRAWINGS

FIGS. 1A–B show the ability of monocyte-associated HIV-$1_{Ba-L}$, PBL (peripheral blood lymphocyte)-associated $HIV_{Ba-L}$ and cell-free virus to cross an epithelial cell monolayer.

FIGS. 2A–B show the transmission of HIV-infected monocytes over time (A) and with varying innoculum cell number (B).

FIG. 3 demonstrates that a human cervical epithelial cell monolayer provides a barrier to cell-free HIV-1 transmission from monocyte-associated HIV-1, PBL-associated HIV-1, or cell-free virus.

FIGS. 4A–B demonstrate that anti-ICAM-1 antibody blocks the transmission of monocyte-associated HIV-1. Anti-ICAM-1 antibodies blocked monocyte-associated HIV-1 transmission (4A) while antibodies directed to the beta subunit of LFA-1, E-cadherin, CD103, and isotype controls did not block transmission (4B).

FIG. 5 demonstrates that anti-ICAM-1 antibody prevents vaginal transmission of infection by cell-associated HIV in vivo. Vaginal transmission of HIV in Hu-PBL-SCID mice was completely blocked by anti-ICAM-1 monoclonal antibodies.

FIGS. 6A–B demonstrate that 293T cells do not express LFA-1. Transepithelial transmission of HIV by HIV-transfected 293T cells expressing neither ICAM-1 nor LFA-1 were blocked by anti-ICAM-1 antibodies showing that preventing HIV transmission at the site of exposure does not require the binding of ICAM-1 with LFA-1.

DETAILED DESCRIPTION OF THE PREFERRED EMBODIMENTS

Most newly acquired cases of HIV-1 infection result from sexual, primarily heterosexual, transmission. While mechanical barriers, such as condoms, can be very effective in preventing sexual transmission, this male-dependent method of protection is frequently not accepted or is impractical for use by the women at greatest risk. In most cases, women at highest risk for new HIV infections are from developing countries. The rapid spread of HIV-1 infection in Africa and Southeast Asia, however, has added new urgency to the need for prophylactic intervention to prevent STD transmission.

In accordance with the present invention, compositions and methods for blocking the transepithelial transmission of the human immunodeficiency virus in an animal using an ICAM-1 agonist/antagonist, at the site of exposure to the virus, are provided. The term "ICAM-1 agonist/antagonist" refers to a compound or bio-molecule capable of blocking or stimulating events associated with the normal function of ICAM-1. The term "site of exposure" refers to the portion of a body of an animal where exposure to HIV occurs, e.g., genital tract, oral cavity, rectum, ocular tissue, auricular tissue, skin etc. The blocking of HIV transmission according to the present invention does not require blocking the binding of ICAM-1 to LFA-1.

In a preferred embodiment, the ICAM antagonist is provided to a mucosal surface of an animal including, but not limited to, the genital, vaginal, rectal, oral or gastrointestinal surfaces. Mucosal surfaces represent potential sites of exposure for HIV through sexual contact, from mother-to-infant, and other mechanisms. The ICAM agonist/antagonist may be applied to a substrate such as a condom or intrauterine device or provided in a variety of forms including, e.g., vaginal wash, lubricant, spermicide, douche, suppository, breast milk supplement, or infant formula.

Antibodies are a versatile prophylactic intervention particularly suited for application to a variety of sites in the body, and in particular, to mucosal surfaces. The antibodies of the invention are directed to modulating the function of ICAM-1 in the etiology of an HIV infection. Other agonists/antagonists, e.g., antisense nucleotide sequences, and ribozymes, may also be used to modulate the function of ICAM-1. Antibodies are an example of a highly specific microbicide capable of prophylactic use in disease prevention. Mucosal antibodies are of particular interest because they generally function by excluding pathogens from the epithelium. Moreover, it is the versatility of the antibody structure to create a virtually inexhaustible repertoire of antigen binding specificities that is important for producing specific microbicides directed to a particular pathogens.

The term "antibodies" herein refers to the spectrum of human, humanized animal, or plant-derived humanized immunoglobulins ("Ig") including, but not limited to, IgG, IgM, IgA, IgE, and fragments, e.g., monovalent, bivalent, and multivalent fragments. Preferred antibodies include bivalent IgG and multivalent IgA human monoclonal antibodies produced in plants ("plantibodies"). Another preferred antibody is an anti-human ICAM-1 IgG1. The plantibody system can readily be used to generate large quantities of antibodies of a given specificity. Antibodies of specific valency, class, and, in the case of IgA, containing secretory component, can be produced in corn plants.

Expression of polymeric and secretory IgA in plants is preferred to more conventional hybridoma techniques for several reasons. The production of sIgA in plants is a single cell system, whereas two different cell types are required in mammalian production systems. The plantibody system has a polymeric IgA scaffold for inserting the cDNA from existing well-characterized antibodies. Plantibodies also have greater stability and are less subject to mutagenesis than antibodies generated and maintained in cell culture. Plants capable of producing plantibodies have a greater long term storage capacity than conventional hybridoma cell lines and can reduce the cost of manufacturing by three to six orders of magnitude. In addition, plantibodies are infinitely scalable, i.e., from a single plant to thousands of acres and avoid safety concerns arising from potential viral contamination of cell cultures.

Another preferred antibody type is sIgA, a common antibody at mucosal surfaces, including the vagina and cervix. This antibody is distinguished functionally from antibodies of the IgG class by the absence of Fc receptors for IgA on most phagocytic cells and by the inability of sIgA to fix complement by the classical pathway. These properties reduce the pro-inflammatory potential of sIgA, a useful characteristic at sites, such as the gastrointestinal tract or bronchioles, where inflammation may result in functional impairment. The reduced Fc receptor and complement binding capacity of sIgA render this class of immunoglobutin less likely to induce the enhancement of infection that has been associated with some HIV-1 specific IgGs. IgA is also distinguished from IgG by its unique reactivity with epithelial cells, which is mediated by the polymeric Ig receptor(s) expressed on the basolateral surface of epithelial cells. In its dimeric form, IgA attaches to these receptors on epithelial cells which permits the antibody molecule, and any antigen attached to it, to trancytose the epithelial cell without undergoing degradation. A portion of the receptor remains attached to the IgA molecule after it leaves the epithelial cell, giving rise to the secretory piece of IgA. The functional component of the polymeric Ig receptors is highly conserved among different species, including mice and humans.

In another preferred embodiment, a prophylactic pharmaceutical composition comprising an ICAM-1 agonist/antagonist and a pharmaceutically acceptable carrier is provided. A "pharmaceutically acceptable carrier" refers to a carrier or vehicle suitable for application to a mucosal surface. The ICAM-1 agonist/antagonist may be formulated in any appropriate carrier, provided that the antagonist and carrier are compatible. The activity of the antagonist should not be diminished by the carrier to the extent it no longer blocks transmission of HIV. The carrier can be aqueous, or non-aqueous, for example, alcoholic or oleaginous, or a mixture thereof, and may additionally contain other surfactants, emollients, lubricants, stabilizers, dyes and active ingredients such as preservatives, antibiotics, contraceptives, spermicides or pharmaceutical agents. The compositions can be in the form of, e.g., creams, foams, lotions, ointments, solutions, solids and sprays.

Preferred carriers are suitable for application to the vaginal tract, oral cavity, gastrointenstinal tract, and rectum. Particularly preferred carriers are mucoadhesive gels. Suitable carriers may comprise organic solvents, emulsifiers, gelling agents, moisturizers, stabilizers, wetting agents, time release agents, sequestering agents, dyes, perfumes and other components commonly employed in pharmaceutical compositions for administration to mucous membranes.

The compositions of the invention may be provided in vaginal washes or douches for vaginal application. Breast milk supplements and infant formula containing ICAM-1 agonist/antagonists are preferred for providing the ICAM-antagonists to infants through the oral mucosal surface.

Solid dosage forms include suppositories, powders, and granules. In solid dosage forms, the compositions may be admixed with at least one inert diluent such as sucrose, lactose, or starch and may additionally comprise lubricating agents, buffering agents, and other components well known to those skilled in the art.

Actual dosage levels of the ICAM-1 agonist/antagonist in the methods, compositions, and articles of the invention may be varied to obtain amounts at the site of exposure to the virus or point of entry to obtain the desired prophylactic response. Accordingly, the selected dosage level will depend on the nature and site of exposure to the virus or point of entry, the desired prophylactic response, the route of administration, the desired duration of the prophylaxis and other factors.

The preferred agonist/antagonist for the compositions, articles and methods of the present invention is an anti-ICAM-1 antibody. Effective concentrations of antibodies are generally in the range of about 20 to about 1000 µg/ml, although the concentration may be varied depending on the particular circumstances. The dosage level of anti-ICAM-1 plantibodies may extend to about to 10 mg/ml.

The ICAM-1 agonist/antagonists of the invention are administered by any suitable method. Preferable, the ICAM-1 agonist/antagonists are topically applied prophylactically to mucosal surfaces for the prevention of HIV transmission. Preferably, the anti-ICAM-1 antibodies are delivered in a mucoadhesive gel vehicle that retains immunoglobulin activity for a period of one to several days.

The agonist/antagonists of the invention may also be delivered via a genetically-modified bacteria capable of producing an anti-ICAM-1 agonist/antagonist, e.g., anti-ICAM-1 antibody, anti-ICAM-1 antisense, ICAM-1 antigen, or ribozyme. A "genetically-modified" bacteria contains or is transfected with a plasmid DNA vector or other vector, e.g. viral, naked DNA or RNA, comprising nucleotides encoding an anti-ICAM antibody, anti-ICAM antisense nucleotide sequence, or ribozyme. Preferred genetically-modified bacteria are species that are part of the natural flora of the mucosal surface of interest, i.e. genital tract, oral cavity etc. The genetically-modified bacteria may be created using any suitable recombinant DNA or other method known to those of skill in the art.

In another preferred embodiment, an article of manufacture comprising a substrate and an ICAM-1 agonist/antagonist is provided. The term "support" or "support" refers to an object, e.g., sponges, condoms, diaphragms, intrauterine devices, or cervical rings capable of being impregnated with or coated with an ICAM-1 agonist/antagonist and delivering the ICAM-1 agonist/antagonist to mucosal surfaces of the body. Condoms, for example, may be coated by spraying the antagonist onto the surface of the condom, or by impregnating the antagonist into the condom during manufacture by processes known in the art. Baby bottle nipples may also be coated in a similar fashion. In another preferred embodiment, the anti-ICAM-1 antibodies are delivered in a slow-release product such as a cervical ring impregnated with the antibodies.

Because HIV is primarily transmitted through sexual activity, a preferred method of the invention comprises contacting the agonist/antagonistic compositions of the invention with vaginal epithelium or other mucosal surfaces during or prior to sexual activity. Preferably, a contraceptive device, such as a condom coated or impregnated with the ICAM-1 agonist/antagonist, or a topical composition such as a gel or foam is used in sufficient quantity to prevent HIV transmission and infection. The compositions may be combined with a spermicide when the added benefit of the prevention of pregnancy is desired.

In yet another embodiment of the invention, the ICAM-1 agonist/antagonists are affixed to a solid surface, e.g., plastic, or a similar material for delivery to the site of exposure to HIV. Suitable plastics include, for example, polyvinylchloride, polyethylene, polyurethane or silicon and other common substances for containers and baby bottles. Baby bottles, including the nipple assembly, or other containers and conduits for biological fluids may be coated with ICAM-1 agonist/antagonists in sufficient quantity to prevent or block cell-associated HIV transmission. The agonist/antagonist may also be incorporated during the polymerization of the plastic polymer and leach out of the surface in a time-release fashion.

The ability of particular ICAM-1 agonist/antagonists and compositions to block transepithelial transmission of HIV may be evaluated, for example, in a transwell culture system. A preferred transwell system contains an insert which divides wells from 24-well plates into upper and lower chambers separated by a removable mesh containing pores that are 5 m in diameter. A human cervical epithelial cell line such as ME180 (American Type Culture Collection, Rockville, Md.) is grown to confluence on the removable mesh. The confluent epithelial cells form a barrier which is impermeable to $C^{14}$-inulin and, selectively favors transmission of macrophage-, as opposed to peripheral blood lymphocyte (PBL)-associated virus. HIV transmitted across the epithelial barrier will appear in the lower chamber of the transwell system. Thus, an ICAM-1 agonist/antagonist can be evaluated for its ability to block the transmission of HIV across the mesh supporting the confluent epithelial cell barrier. The transwell system permits rapid and direct examination of the ability of Mabs of different specificities to block transmission of cell-associated HIV-1 across epithelial cell monolayers. Such a system can be used to compare the relative efficacy of antibody classes and isotypes, as well.

ICAM-1 agonist/antagonists may also be evaluated in an in vivo animal model that closely resembles the setting in which transmission actually occurs. For example, the Hu/PBL-SCID mouse vaginal transmission model is an excellent model for studying HIV-1 transmission. The activation state of transplanted human PMBC cells within the mouse at the time of infection (8–10 days post human cell implantation) is similar to that observed in human peripheral blood mononuclear cells (PBMC) and markedly different from that observed in tissue culture typically used for growing HIV. Furthermore, phylogenetic analysis of variants transmitted to Hu-PBL-SCID mice indicate that viral transmission is not random and that subsets of macrophage tropic viral variants are preferentially transmitted. This transmission pattern duplicates the human setting in which a very restricted range of macrophage-tropic viruses from the donor are transmitted to the recipient. ICAM-1 agonist/antagonists may be applied, for example, to the vaginal tract of Hu-PBL-SCID mice exposed to HIV to evaluate the ability of the ICAM-1 agonist/antagonist to block HIV transmission in vivo.

Application of the teachings of the present invention to a specific problem or environment are within the capabilities of one having ordinary skill in the art in light of the teachings contained herein. Further examples of the products of the present invention and processes for their use appear in the following examples.

EXAMPLE 1

Isolation of Cell-Free HIV and HIV-Infected Peripheral Blood Lymphocytes and Monocytes HIV-$1_{Ba-L}$ (Advanced Biotechnologies Inc., Columbia, Md.), a macrophage-tropic, NSI, CCR5-utilizing variant of HIV-1 was purchased in 1.0 ml aliquots ($1 \times 10^6$ fifty percent tissue culture infectious doses ($TCID_{50}$)/ml) and stored in liquid nitrogen. Virus stocks were thawed once prior to use in culture.

Human PBMC were isolated by centrifligation of leukopheresed blood on Ficoll Hypaque (Pharmacia, Piscataway, N.J.). Total PBMC were plated in 75 or 150 cm$^2$ tissue culture flasks (Corning Scientific Products, Inc., Cambridge, Mass.) at $1 \times 10^7$/ml in RPMI-1640 supplemented with 100 U/ml penicillin/100 mcg streptomycin, 10 ng/ml gentamicin, and 2 mM L-glutamine (media and all supplements from Life Technologies, Grand Island, N.Y.). Cells were resuspended in RPMI-1640 as described above (hereafter referred to as cRPMI) with 20% heat-inactivated FCS (56°C for 45 min, Gemini Bio-Products, Inc. Calabasas, Calif.) and 10% heat-inactivated, A/B human serum (HS; Nabi, Boca Raton, Fla.) during the initial 12 h of culture. Monocytes were collected. Non-adherent PBMC were removed and discarded; adherent cells were removed from the flasks using cold HBSS (Life Technologies). Adherent cells were determined to be >95% monocytes by expression of the surface antigen CD14 (FITC-labeled, anti-human CD14 antibody, My-4; Coulter Immunotech, Hialeah, Fla.). Monocytes were washed and resuspended at $5 \times 10^6$/ml with $1 \times 10^3$ TCID., of HIV-$1_{Ba-L}$ in 5 ml of cRPMI-10% FCS or cRPMI-10% HS in 25 cm$^2$ flasks (Corning Scientific Products, Inc.), and cultured at 37° C., 5% $CO_2$. The virus inoculum was removed after 24 hours, cells were washed once with warm cRPMI, and fresh cRPMI-10% FCS or cRPMI-10% HS was added. Cultures were fed with fresh media on days 3 and 7 post-infection (pi). Monocytes were removed from the flasks using cold HBSS or 0.02% EDTA (Sigma Chemical Co., St. Louis, Mo.), and used for experiments on day 10 pi.

PBL (Peripheral Blood Lymphocytes) were resuspended at $2 \times 10^6$/ml in cRPMI-10% FCS supplemented with PHA (5 µg/ml, Sigma) for 48 h. Following infection with $1 \times 10^3$ $TCID_{50}$ HIV-$1_{Ba-L}$, PBL were cultured identically to monocytes except that the PBL culture media contained 10 U/ml IL-2 (Boehringer Mannheim, Indianapolis, Ind.). The extent to which the monocytes and PBL were infected with HIV-1 was determined by limiting dilution PCR performed with appropriate standards and controls as described previously using HIV-1 gag-specific primers (forward primer, 5'-GCG-AGA-GCG-TCA-GTA-TTA-AGC-GG-3', and reverse primer, 5'-TCT-GAT-AAT-GCT-GAA-AAC-ATG-GG-3'). PCR products were visualized by electrophoresis on a 1% agarose gel.

Cell-free virus was derived from HIV-$1_{Ba-L}$-infected monocytes or HIV$_{Ba-L}$-infected PBL in cRPMI-10% FCS or cRPMI-10% HS. Supernatants were cleared of cells by centrigation and filtered through a 0.2 µm syringe filter (Millipore, Bedford, Mass.). Cell-free virus was quantitated by HIV p$^{24}$ ELISA (Dupont NEN, Boston, Mass.) and by co-culture with PBMC from a healthy, HIV-negative donor to determine $TCID_{50}$.

EXAMPLE 2

Human Cervical Epithelial Cell Transwell Cultures

The human, spontaneously-transformed, cervical epithelial cell line, ME-180 (ATCC, Rockville, Md.), was cultured in 75 cm$^2$ flasks in cRPMI-10% FCS and routinely subcultured every 3 days with cell displacement by 0.05% trypsin-EDTA (Life Technologies). ME-180 cells were plated at $2 \times 10^5$ in 0.1 ml cRPMI-10% FCS or 10% HS per 5.0 µm, 12 mm diameter transwell insert (Corning Scientific Products, Inc). ME-180 cells in the transwells were maintained at 37° C., 5% $CO_2$ conditions. Media was changed every 2–3 days. The cells form a polarized, complete monolayer on the transwell inserts in 7 days, which was confirmed by monitoring the resistance across the epithelium using an ohmmeter (Millipore) and staining with a fluorochrome-labeled antibody against ZO1, a protein found at epithelial tight junctions (20) (1:50 dilution, Zymed, San Francisco, Calif.). The ME-180 monolayers on inserts were always used for experiments between days 7 and 10 of culture.

EXAMPLE 3

Transepithelial Migration and HIV-1 Transmission

The transepithelial migration assay was performed as described by Bomsel, with several alterations. Briefly, $1 \times 10^6$ $HIV_{Ba-L}$-infected monocytes, $1 \times 10^6$ $HIV_{Ba-L}$-infected PBL, or cell-free HIV-1 in the supernatant fluid from the monocyte or PBL cultures, were added to the apical sides of epithelial monolayers. Timecourse analyses were performed, with collection of the apical and basal side media between one and 48 h after the addition of the infected cells to the inserts. Nearly maximal transmission across the monolayer was observed at 24 hours and this time-point was chosen for all subsequent experiments. Viability of monocytes and PBL was assessed by trypan blue exclusion (Sigma) prior to the addition of the cells to the transwells and after the 24 hour transmission period, and was always found to be >90%. HIV-1 p24 antigen ELISA assays (Dupont NEN) were performed to quantitate the amount of HIV-1 p24 antigen in the apical and basal supernatant fluid (sensitivity of 12.5 pg/ml–350 pg/ml).

EXAMPLE 4

Transmission Blocking Studies

Mouse anti-human ICAM-1 antibody (20 μg/ml and dilutions; HA58 (IgG1), Pharmingen), anti-human E-cadherin antibodies (20 μg/ml; 67A4 (IgG1) Coulter Immunotech, and E4.6 (IgG1)), anti-human CD103 antibodies (20 μg/ml; 2G5 (IgG2a), Coulter Immunotech and αE7-1 (IgG2a), αE7-2 (IgG1) and αE7-3 (IgG1)), and anti-human CD18 antibody (20 μg/ml; L130 (IgG1), Becton Dickinson), or their respective isotype controls, were added to $1 \times 10^6$ HIV-infected monocytes or HIV-infected 293T cells with or without ICAM-1, moments prior to their addition to the ME-180 transwell cultures. The highest concentration of antibody (20 μg/ml) was chosen following the criteria established by the AIDS Clinical Trials Group (ACTG) Antibody Selection Working Group for an antibody demonstrating efficacy at a concentration below that which is achievable in vivo (20–25 μg/ml). Apical and basal supernatant fluids were collected after 24 hours incubation at 37° C., 5% $CO_2$. HIV-1 p24 antigen was quantitated by ELISA.

EXAMPLE 5

Monocyte-Associated HIV-1 Crosses Human Cervical Epithelial Cells More Efficiently than PBL-Associated HIV-1 or Cell-Free Virus HIV-1-infected monocytes, HIV-1-infected PBL, or cell-free virus (cfv) derived from monocyte or PBL cultures, each in cRPMI with 10% FCS, were placed into the apical chambers of transwell cultures containing a confluent monolayer of ME-180 epithelial cells. The extent to which monocyte-associated, PBL-associated, or cell-free virus crossed the intact, human cervical epithelial monolayer was evaluated (FIG. 1A). (cRPMI-10% FCS culture media (n=8 donors, ap<0.05 comparing mono and PBL, and between PBL and cfv; bp<0.001, comparing mono and cfv). Results are expressed as the concentration of HIV-1 p24 antigen (pg/ml) from the basal supernatant fluid of transwell cultures of ME-180 and the respective inoculum.

Monocyte-associated virus was roughly five times more efficient at crossing the cervical epithelium than PBL-associated virus. Cell-free virus derived from either cell type did not efficiently cross the epithelial monolayer, and was usually below the detectable limits of the p24 ELISA assay.

Figure 1B:
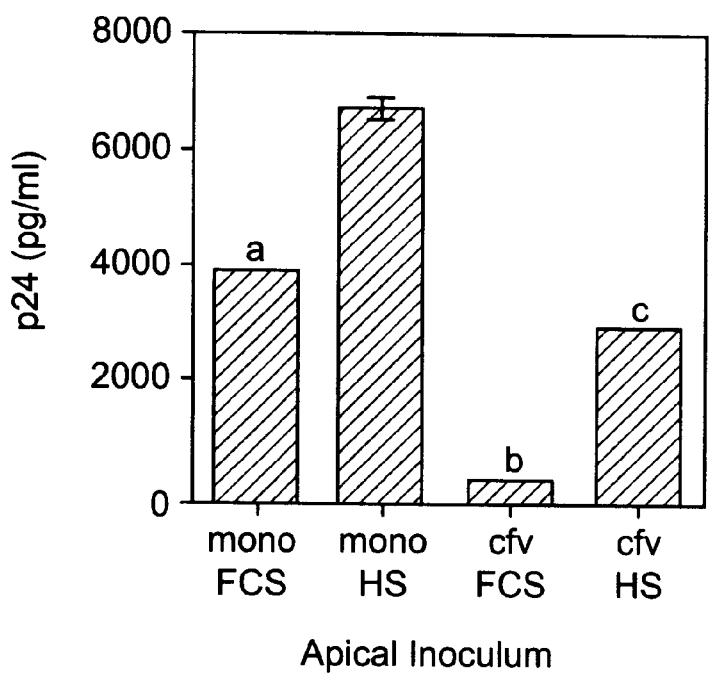

To address whether cell-free HIV-1 may be inhibited from crossing an epithelial monolayer by glycoproteins found in FCS (fetal calf serum) as suggested by Kage and colleagues, studies were performed using HIV-infected monocytes or cfv (cell-free virus) that had been cultured in cRPMI containing 10% HS. In these experiments, monocyte-associated HIV-1 cultured in cRPMI-10% HS crossed the epithelium more efficiently than monocyte-associated virus cultured in cRPMI-10% FCS, and more efficiently than cfv in cRPMI-10% FCS or –10% HS (FIG. 1B) (cRPMI-10% FCS or HS culture media (representative experiment of n=3, ap<0.05 comparing between mono FCS and mono HS, bp<0.05 comparing between cfv FCS and cfv HS, and cp<0.005 comparing between mono HS and cfv HS)). In contrast to the transepithelial transmission measured in 10% FCS, cfv cultured in cRPMI-10% HS was able to cross the intact epithelium, although at a significantly lower level than cell-associated virus (p<0.05) (FIG. 1B).

The apical supernatant fluid was evaluated at several points in time for HIV-1 p24 antigen to determine the extent to which virus was shed from infected monocytes or PBL inoculated onto the apical side of the epithelium. The concentration of p24 antigen in supernatant fluid from HIV-infected monocytes and HIV-infected PBL cultured in either FCS or HS was always comparable and did not differ significantly over the course of infection (data not shown).

The HIV-1 measured in the basilar supernatant (indicated by p24 concentration) was found to be infectious when, upon co-culture with uninfected monocytes or PHA-stimulated PBL, there was an increase in the amount of p24 antigen in the cultures over time (data not shown).

EXAMPLE 6

Figures 2A, 2B:
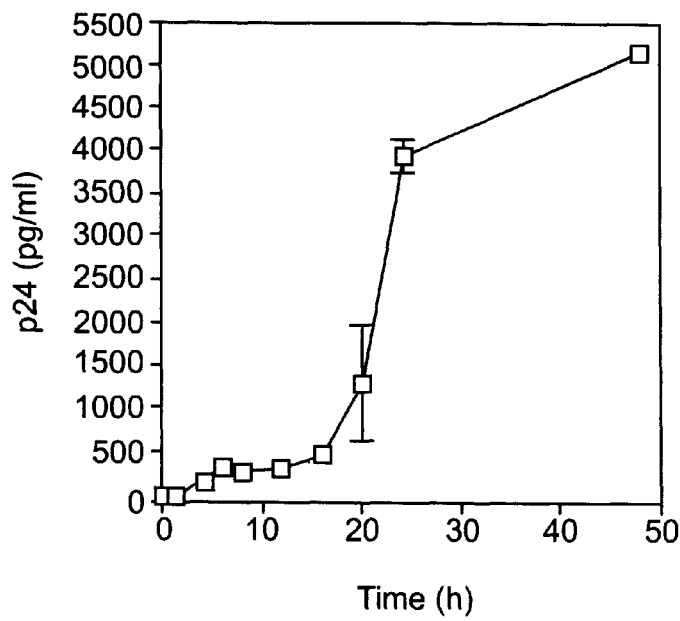

Monocytes Cross the Cervical Epithelium in a Time- and Dose-Dependent Manner Transwell cultures with ME-180 monolayers were established and $1 \times 10^6$ HIV-infected monocytes in cRPMI-10% HS were added to the apical side of the epithelium to analyze the kinetics of transepithelial transmission. Infected monocytes that have migrated and/or transmitted HIV-1 transepithelially were detected as early as 4 hours (FIG. 2A) with increasing basilar p24 levels until 48 hours, when a plateau was reached. Similarly, $1 \times 10^6$ cells, or fivefold dilutions thereof, were added to the apical side of the epithelium and the basal-side supernatant fluid was sampled for the presence of p24 antigen to determine the minimal cell inoculum required to detect virus on the basilar side of the epithelium. HIV-1 p24 antigen was consistently detected in the basal medium after applying 5,000 HIV-infected monocytes. Between 1–5% of this population of cells are infected with HIV-1 as determined by LD-PCR (data not shown) so this means as few as 500 infected cells consistently transmitted HIV-1. Detectable p24 from the basal side supernatants was obtained with as few as 1,000 monocytes applied to the apical side of the transwell (with the same 1–5% infection rate) (FIG. 2B).

The experiments depicted in FIG. 2 were performed with HIVBa-L-infected monocytes in cRPMI-10% HS. The results are expressed as the concentration of HIV-1 p24 antigen (pg/ml) in the basal supernatant. A representative experiment for timecourse (n=4) and inoculum dose (n=2) is shown. +basilar p24 between 100–1,000 pg/ml; ++basilar p24 between 1,001–5,000 pg/ml, +++basilar p24 between 5,001–30,000 pg/ml, –basilar p24 below limit of detection (12.5 pg/ml).

EXAMPLE 7

The Intact Human Cervical Epithelium Limits HIV-1 Transmission

Figure 3:
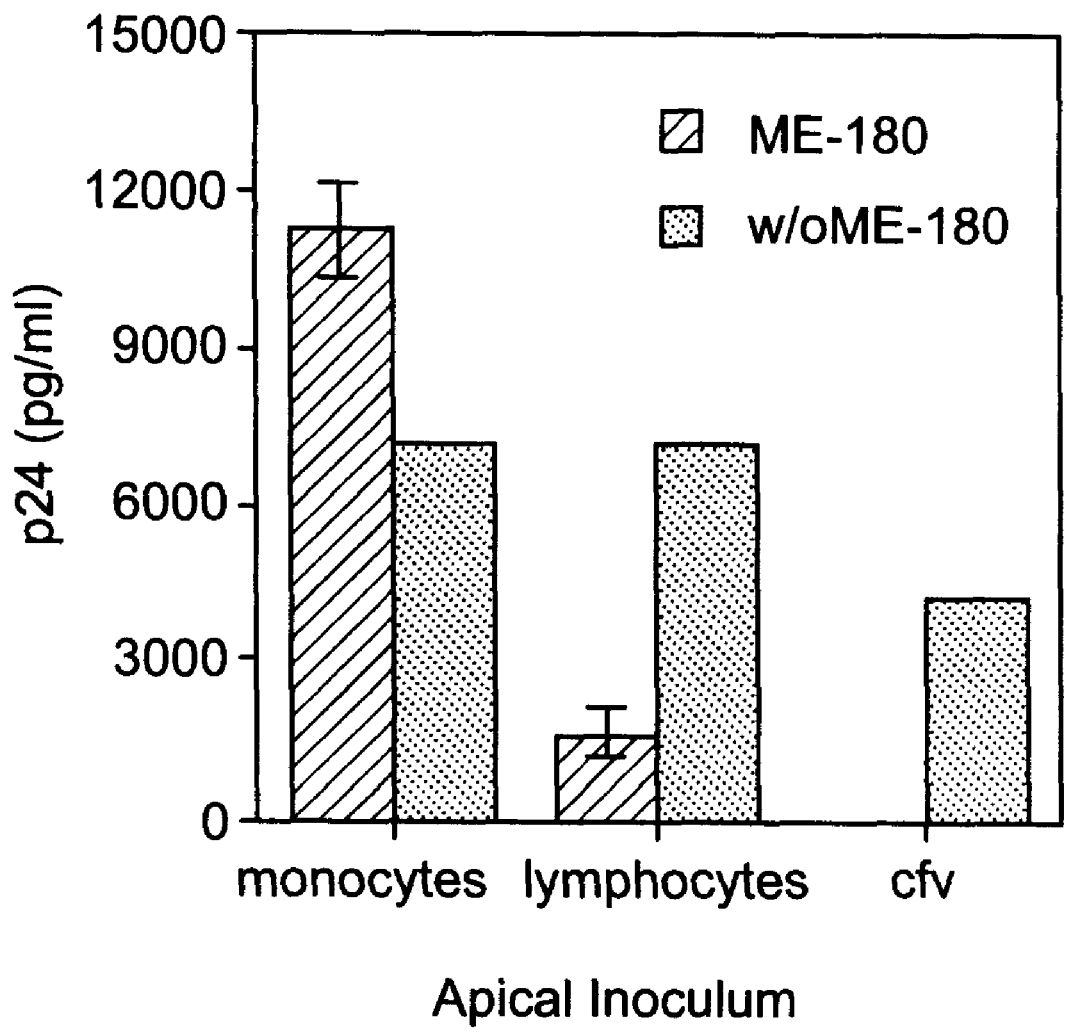

It has been shown previously that the human cervical epithelial cell monolayer within the transwell insert forms a complete, polarized surface and provides a definitive barrier to cell-free HIV-1. The following experiment was performed to determine the extent to which the cervical epithelial monolayer and the membrane dividing the transwell chamber provided a barrier that limited the transepithelial transmission of HIV-1. To do so, the p24 antigen concentration in the lower chamber media of transwells without ME-180 cells present was measured. In contrast to the different levels of basal HIV-1 p24 antigen transmitted by HIV-infected monocytes or HIV-infected PBL shown in FIG. 1, the amount of p24 antigen measured in the lower chamber of the transwell cultures without cervical epithelial cells did not differ significantly (p>0.005) between monocyte-associated HIV-1, PBL-associated HIV-1, or cell-free virus (FIG. 3). These data suggest that the membrane composition and pore size does not limit the transmission of HIV-1, but rather, it is the tight junctions of the epithelial layer and the putative interactions between HIV-infected cells and the epithelium that determine the extent to which transepithelial HIV-1 transmission occurs.

The data shown in FIG. 3 are expressed as p24 antigen (pg/ml) in the basal side or lower chamber supernatant fluid from the transwell cultures with and without ME-180 epithelial cells plated on the insert membranes, respectively. A representative experiment (of n=3) is shown, p<0.05 comparing within inoculum groups either with and without ME-180, p>0.05 comparing between inoculum groups without ME-180.

EXAMPLE 8

Anti-ICAM-1 Antibodies Block Monocyte-Associated HIV-1 Transmission

To examine whether the adhesion interaction between HIV-infected monocytes and epithelial cells was critical for transepithelial migration and HIV-1 transmission, antibodies against several adhesion molecules were added to the transwell cultures. Antibodies to ICAM-1, CD18, E-cadherin, or the alphaE-beta7 integrin (CD103) (between 1–20 µg/ml) were added at the same time as HIV-infected monocytes and remained in the cultures for the duration of the experiment. The antibodies were chosen to target specific ligand-receptor interactions previously shown to be involved in immune cells binding to epithelial cells.

Figure 4A:
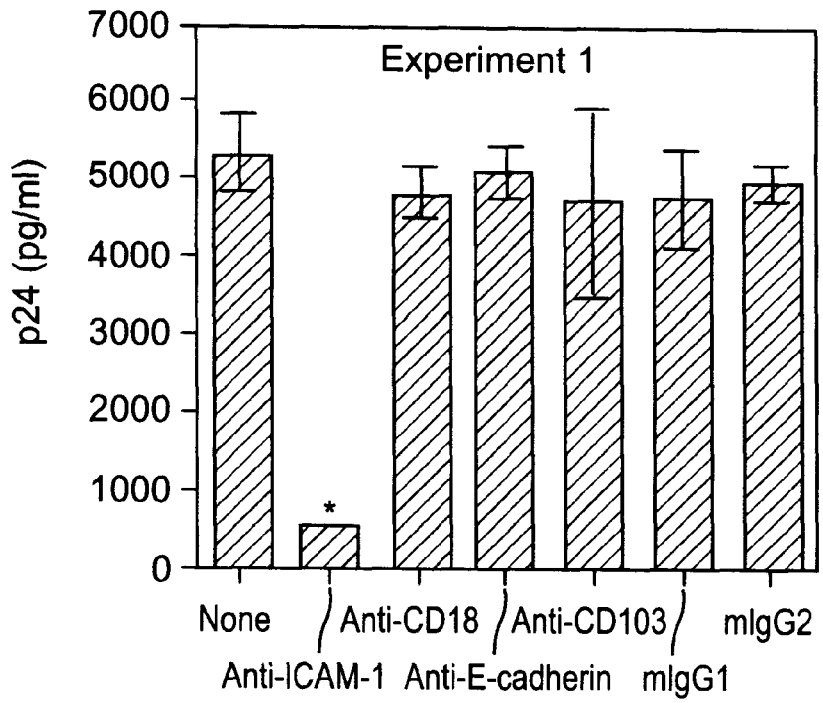

ICAM-1 is expressed on HIV-infected monocytes, and on epithelial cells. Anti-ICAM-1 antibodies blocked the transmission of monocyte-associated HIV-1, as measured by the amount of p24 antigen on the basal side of the epithelial monolayer (FIG. 4A). The CD18 molecule is the β-subunit of lymphocyte function-associated antigen LFA-1, which binds to ICAM-1 and is involved in HIV-induced syncytium formation. Anti-CD18 and the respective isotype controls, did not block transepithelial transmission of HIV-1 (FIG. 4A).

Figure 4B:
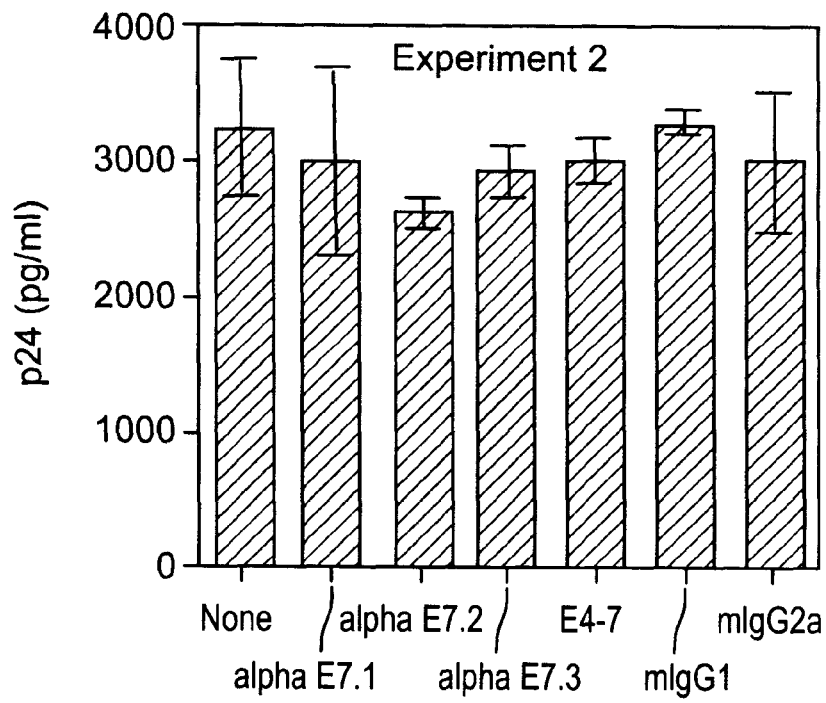
Figure 5:
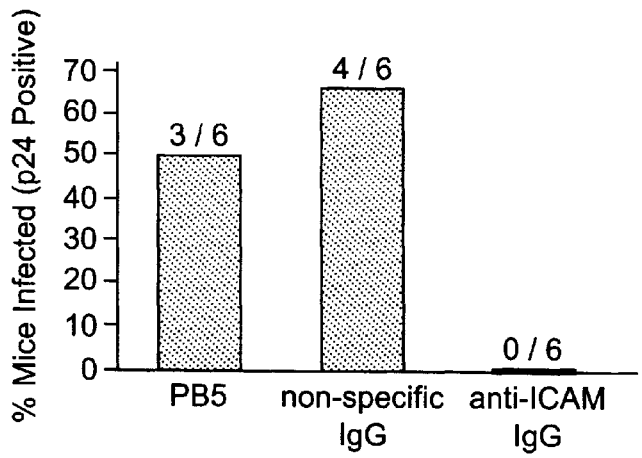

To determine whether the inhibition of transepithelial transmission was specific to the ICAM-1:LFA-1 interaction, antibodies against E-cadherin and CD103 were tested for their ability to inhibit HIV-1 transmission in the transwell system. E-cadherin is expressed on epithelial cells and its ligand, CD103, is expressed on monocytes and a subset of PBL. Anti-E-cadherin antibodies, anti-CD103 antibodies, and their respective isotype controls did not block the transepithelial transmission of HIV-1 (FIGS. 4, A and B). It was determined that incubation of HIV-infected monocytes with the antibodies used in these experiments did not alter the amount of virus released from the infected cells, as measured in the apical supernatant fluid after the 24 hour incubation period (data not shown). Anti-E-cadherin (20 mg/ml), anti-CD103 (20 mg/ml), anti-CD18 (LFA-1) (20 mg/ml), murine IgG1 (20 mg/ml) and murine IgG2a (20 mg/ml) antibodies added with infected monocytes to the transwell cultures have no effect on the transepithelial transmission of HIV-1. The results of FIG. 4 are expressed as HIV-1 p24 antigen from the basal side supernatant fluid with a p<0.05.

EXAMPLE 9

Mab Against ICAM-1 Inhibits HIV-1 Vaginal Transmission in Hu-PBL-SCID Mice

Monoclonal antibodies can be protective against HIV-1 in the Hu-PBL-SCID mouse as shown in three previous studies. However, none of these studies were directed to anti-ICAM-1 antibody or addressed the issue of protection against vaginal transmission of virus. In all cases the Mab was effective against viruses carrying the specific epitopes against which the Mab was raised, but was not cross-protective against a heterologous HIV-1 variant.

As can be seen in Table 1, vaginally applies Mab to ICAM-1 completely blocked vaginal transmission of cell-associated HIV-1 in the SCID mouse model. The results are statistically significant (p=0.03, one tailed Fisher exact test; p=0.06, two tailed Fisher exact test).

TABLE 1

| Mab Administered Prior to Cell Challenge | Mice infected/Mice challenged |
| --- | --- |
| Anti-ICAM-1 | 0/6 |
| Control IgG1 Mab | 4/6 |

EXAMPLE 10

Blocking Transepithelial Transmission of Cell-Associated HIV Does not Require Blocking the Binding of ICAM-1 to LFA-1

Transfection of 293T cells which do not express ICAM-1 on their surface was performed to determine if blocking of transepithelial transmission of cell-associated HIV required blocking the binding of ICAM-1 to LFA-1. The results indicate that transfected 293T cells could transmit HIV-1 across the epithelial cell barrier and that this transmission, as measured by the concentration of HIV-1 p24 antigen in the basilar compartment of the transwell, could be blocked by antibody to ICAM-1 (Table 2).

TABLE 2

| Transfected Cells | Anti-ICAM-1 Antibody | P24 in Lower Chamber of Transwell after 24 hours (pg/ml ± SD |
|---|---|---|
| 293T-no ICAM-1 | None | 9087.5 ± 303.35* |
| 293T-no ICAM-1 | 20 ug/ml | 2075 ± 50.91* |

*p < 0.001 comparing the difference in p24 concentrations

Figure 6A:
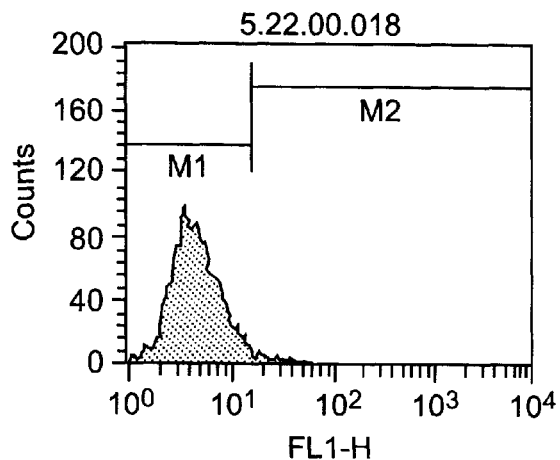
Figure 6B:
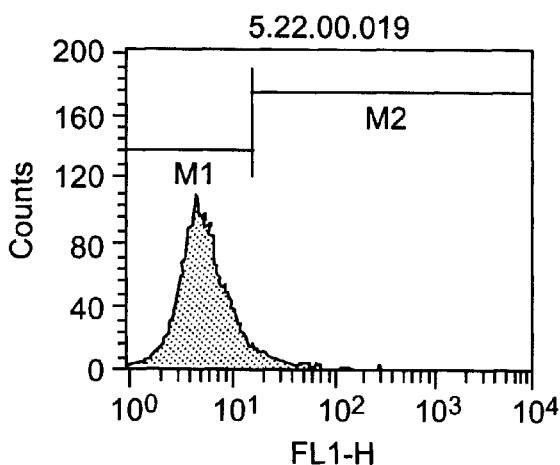

Since ICAM-1 was not present on the surface of 293T cells (data not shown), the ability of anti-ICAM-1 antibody to block transmission had to be through interactions with ICAM-1 on the surface of the ME180 cervical epithelial cell line, which is known to express ICAM-1. Flow cytometry confirmed that the 293T cells do not express LFA-1 (FIGS. 6A–B). Since 293T cells lack LFA-1, the anti-ICAM-1 antibody cannot be blocking transmission by blocking interactions between ICAM-1 and its counter-receptor, LFA-1.

EXAMPLE 11

No Vaginal Inflammatory Response from Anti-ICAM-1 Mab

One potential concern is that intravaginal administration of Mab's directed against ligands that play a role in the immune response might stimulate a local inflammatory response. To address this question, we administered twice daily for 14 days to normal BALB/c mice intravaginal inocula of 20 mg/ml of IgG2a Mab directed against mouse ICAM-1, 20 mg/ml of an irrelevant IgG2a Mab, or 5 mg lipopolysaccharide from *Salmonella typhimurium*. Anti-ICAM-1 Mabs showed no toxicity in treated mouse vaginal epithelium.

EXAMPLE 12

Mabs are not Absorbed into Serum from Intravaginal Placement

Mabs are not absorbed into the serum from intravaginal placement. This would be of potential clinical concern with the use of Mab directed against host antigens. Three SCID mice were inoculated with 20 mg normal mouse IgG twice daily for ten days. Using an ELISA assay that is sensitive to a level of 0.1 mg/ml, serum from mice were assayed two hours after the most recent injection on days 4, 7, and 10 for increases in concentrations of mouse Ig. Baseline mouse Ig values ranged between 0–4 mg/ml. No increases in mouse antibody concentration were observed in any of the mice at any of the time points assayed.

REFERENCES

1. Fultz, P. N., H. M. McClure, H. Daugharty, A. Brodie, C. R McGrath, B. Swenson, and D. P. Francis. 1986. Vaginal transmission of human immunodeficiency virus (HIV) to a chimpanzee. J. Infect. Dis. 154:896.
2. Burkhard, M. J., L. A. Obert, L. L. O'Neil, L. J. Diehl, and E. A. Hoover. 1997. Mucosal transmission of cell-associated and cell-free feline immunodeficiency virus. AIDS Res. Hum. Retrovir. 13:347.
3. Miller, C. J., N. J. Alexander, S. Sutjipto, A. A. Lackner, A. Gettie, A. G. Hendrickx, L. J. Lowenstein, M. Jennings, and P. A. Marx. 1989. Genital mucosal transmission of simian immunodeficiency virus: animal model for heterosexual transmission of human immunodeficiency virus. J. Virol. 63:4277.
4. Zacharopoulos, V. R, M.-E. Perotti, and D. M. Phillips. 1997. A role for cell migration in the sexual transmission of HIV-1. Curr. Biol. 7:R534.
5. Fortin, J.-F., R Cantin, G. Lamontagne, and M. Tremblay. 1997. Host-derived ICAM-1 glycoproteins incorporated on human immunodeficiency virus type 1 are biologically active and enhance viral infectivity. J. Virol. 71:3588.
6. Fortin, J.-F., R., R. Cantin, and M. Tremblay. 1998. T cells expressing activated LFA-1 are more susceptible to infection with human immunodeficiency virus type 1 particles bearing host-encoded ICAM-1. J. Virol. 72:2105.
7. Rizzuto, C. D., and J. G. Sodroski. 1997. Contribution of virion ICAM-1 to human immunodeficiency virus infectivity and sensitivity to neutralization. J. Virol. 71:4847.
8. Bomsel, M. 1997. Transcytosis of infectious human immunodeficiency virus across a tight human epithelial cell line barrier. Nat. Med. 3:42.
9. D'Souza, M. P., D. Livnat, J. A. Bradac, and S. H. Bridges. 1997. Evaluation of monoclonal antibodies to human immunodeficiency virus type 1 primary isolates by neutralization assays: performance criteria for selecting candidate antibodies for clinical trials. J. Infect. Dis. 175:1056.
10. Kage, A., E. Shoolian, K. Rokos, M. ™zel, R.Nuck, W. Reutter, E. K'ttgen, and G. Pauli. 1998. Epithelial uptake and transport of cell-free human immunodeficiency virus type 1 and gp120 coated microparticles. J. Virol. 72:4231.
11. Fais, S., P. Borghi, G. Gherardi, M. Logozzi, F. Belardelli, and S. Gossani. 1996. Human immunodeficiency virus type 1 induces cellular polarization, intercellular adhesion molecule-1 redistribution and multinucleated giant cell generation in human primary monocytes but not in monocyte-derived macrophages. Lab. Invest. 75:783.
12. Vermot-Desroches, C., D. Rigal, S. Escaich, J. Bernaud, C. Pichoud, J. P. Lamelin, and C. Trepo. 1991. Functional epitope analysis of the human CD11a/CD18 molecule (LFA-1, lymphocyte function-associated antigen-1) involved in HIV-1-induced syncytium formation. Scand J. Immunol. 34:461.
13. Anderson, D. J., and E. J. Yunis. 1983. "Trojan Horse" leukocytes in AIDS. N. Engl. J. Med. 309:984.
14. Levy, J. A. 1988. The transmission of AIDS: the case of the infected cell. J. A. M. A. 259:3037.
15. Collins, K. B., B. K. Patterson, G. J. Naus, D. V. Landers and P. Gupta. 2000. Development of an in vitro organ culture model to study transmission of HIV-1 in the female genital tract. Nat. Med. 6:475.
16. Agracetus. 1994. Plant Bioreactor Systems,. Agraceuts, Inc.
17. Bomsel, M., M. Heyman, H. Hocini, S. Lagaye, L. Belec, C. Dupont, and C. Desgranges. 1998. Intracellular Neutralization of HIV Transcytosis across Tight Epithelial Barriers by Anti-HIV Envelope Protein dIgA or IgM. Immunity. 9:277–287.
18. Bourinbaiar, A. S., and D. M. Phillips. 1991. Transmission of human immunodeficiency virus from monocytes to epithelia. J Acquir Immune Defic Syndr. 4:56–63.
19. Butini, L., A. R. De Fougerolles, M. Vaccarezza, C. Graziosi, D. I. Cohen, M. Montroni, T. A. Springer, G.

Pantaleo, and A. S. Fauci. 1994. Intercellular adhesion molecules (ICAM)-1 ICAM-2 and ICAM-3 function as counter-receptors for lymphocyte function-associated molecule 1 in human immunodeficiency virus-mediated syncytia formation. Eur J Immunol. 24:2191–5.

20. de Fougerolles, A. R., X. Qin, and T. A. Springer. 1994. Characterization of the function of intercellular adhesion molecule (ICAM)-3 and comparison with ICAM-1 and ICAM-2 in immune responses. J Exp Med. 179:619–29.

21. de Fougerolles, A. R., and T. A. Springer. 1992. Intercellular adhesion molecule 3, a third adhesion counter-receptor for lymphocyte function-associated molecule 1 on resting lymphocytes. J Exp Med. 175:185–90.

22. Dustin, M. L., O. Carpen, and T. A. Springer. 1992. Regulation of locomotion and cell-cell contact area by the LFA-1 and ICAM-1 adhesion receptors. J Immunol. 148:2654–63.

23. Fiedler, U., and U. Conrad. 1995. High-level production and long-term storage of engineered antibodies in transgenic tobacco seeds. Biotechnology. 13:1090–1093.

24. Fortin, J. F., R Cantin, G. Lamontagne, and M. Tremblay. 1997. Host-derived ICAM-1 glycoproteins incorporated on human immunodeficiency virus type 1 are biologically active and enhance viral infectivity. J Virol. 71:3588–96.

25. Gauduin, M. C., P. W. Parren, R. Weir, C. F. Barbas, D. R. Burton, and R. A. Koup. 1997. Passive immunization with a human monoclonal antibody protects hu-PBL-SCID mice against challenge by primary isolates of HIV-1. Nat Med. 3:1389–93.

26. Gauduin, M. C., J. T. Safrit, R. Weir, M. S. Fung, and R. A. Koup. 1995. Pre- and postexposure protection against human immunodeficiency virus type 1 infection mediated by a monoclonal antibody. J Infect Dis. 171:1203–9.

27. Hiatt, A., R. Caffertey, and K. Bowdish. 1989. Production of antibodies in transgenic plants. Nature. 342:76–78.

28. Hiatt, A., and J. K.-C. Ma. 1992. Monoclonal antibody engineering in plants. FEBS Letters. 307:71–75.

29. Ma, J. K.-C., A. Hiatt, M. Hein, N. D. Vine, F. Wang, P. Stabila, C. van Dolleweerd, K. Mostov, and T. Lehner. 1995. Generation and assembly of secretory antibodies in plants. Science. 268:716–719.

30. Markham, R. B., D. H. Schwartz, A. Templeton, J. B. Margolick, H. Farzadegan, D. Vlahov, and X. F. Yu. 1996. Selective transmission of human immunodeficiency virus type 1 variants to SCID mice reconstituted with human peripheral blood monoclonal cells. J Virol. 70:6947–54.

31. Marlin, S. D., and T. A. Springer. 1987. Purified intercellular adhesion molecule-1 (ICAM-1) is a ligand for lymphocyte function-associated antigen 1 (LFA-1). Cell. 51:813–9.

32. Milman, G., and O. Sharma. 1994. Mechanisms of HIV/SIV mucosal transmission. AIDS Res Hum Retroviruses. 10:1305–12.

The above description and examples are only illustrative of preferred embodiments which achieve the objects, features, and advantages of the present invention, and it is not intended that the present invention be limited thereto. Any modifications of the present invention which come within the spirit and scope of the following claims is considered part of the present invention.

What is claimed as new and desired to be protected by Letters Patent of the United States is:

1. A method of blocking transepithelial transmission of HIV into an animal comprising providing an anti-ICAM-1 antibody to said animal at the site of exposure to said HIV.

2. The method of claim 1 wherein said anti-ICAM-1 antibody is a plantibody.

3. The method of claim 1 wherein said anti-ICAM-1 antibody is an anti-human ICAM-1 IgG1 antibody.

4. The method of claim 1 wherein said anti-ICAM-1 antibody is provided in amount sufficient to block transepithelial transmission of HIV.

5. The method of claim 4 wherein said amount is in the range of about 20 µg/ml to about 1000 µg/ml.

6. The method of claim 4 wherein said amount is in the range of about 5 mg/ml to about 10 mg/ml.

7. The method of claim 1 wherein said animal is a mammal.

8. The method of claim 1 wherein said animal is a human.

9. The method of claim 1 wherein said anti-ICAM-1 antibody is provided in a form selected from the group consisting of creams, foams, oral solutions, solids, sprays, vaginal washes, vaginal douches, suppositories, breast milk supplements, and infant formula.

10. The method of claim 1 wherein said anti-ICAM-1 antibody is provided in a carrier comprising a material selected from the group consisting of lubricants, surfactants, gels, organic solvents, emulsifiers, gelling agents, moisturizers, stabilizers, wetting agents, time release agents, sequestering agents, dyes, and perfumes.

11. The method of claim 1 wherein said blocking of cell-associated transmission of HIV does not require blocking the binding of ICAM-1 to LFA-1.

12. The method of claim 1 wherein said site of exposure is mucosal surface.

13. The method of claim 12 further comprising innoculating said mucosal surface with genetically-altered bacteria wherein said bacteria are capable of producing an anti-ICAM-1 antibody.

14. The method of claim 12 wherein said mucosal surface is selected from the group consisting of genital, vaginal, rectal, oral, and gastrointestinal surfaces.

15. A method of blocking cell-associated, transepithelial transmission of HIV comprising providing an anti-ICAM-1 antibody to the vaginal epithelium of an animal wherein blocking of said cell-associated transmission of HIV occurs at the vaginal epithelium of said animal.

16. A composition of matter for blocking transepithelial transmission of HIV at the transepithelial site of exposure to said HIV, comprising an anti-ICAM-1 antibody and a vehicle, wherein said anti-ICAM-1 antibody is present in an amount sufficient to block transepithelial transmission of HIV.

17. The composition of matter of claim 16 wherein said amount is in the range of about 20 µg/ml to about 1000 µg/ml.

18. The composition of matter of claim 16 wherein said anti-ICAM-1 antibody is a plantibody.

19. The composition of matter of claim 16 wherein said anti-ICAM-1 antibody is an anti-human ICAM-1 IgG1 antibody.

20. The composition of matter of claim 18 wherein said plantibody is present in amount from about 5 mg/ml to about 10 mg/ml.

21. The composition of matter of claim 16 wherein said composition is a breast milk supplement.

22. The composition of matter of claim 16 wherein said composition is an infant formula.

23. The composition of matter of claim 16 wherein said composition is a vaginal wash.

24. The composition of matter of claim 16 wherein said composition is an oral solution.

25. The composition of matter of claim 16 wherein said composition is a suppository.

26. The composition of matter of claim 16 wherein said composition is an anti-ICAM-1 antibody and said vehicle is a pharmaceutically acceptable carrier.

27. The composition of matter of claim 26 wherein said carrier is selected from the group consisting of lubricants, surfactants, gels, organic solvents, emulsifiers, gelling agents, moisturizers, stabilizers, wetting agents, time release agents, sequestering agents, dyes, and perfiimes.

28. The composition of matter of claim 26 wherein said carrier is a mucoadhesive gel.

29. An article of manufacture for blocking cell-associated, transepithelial transmission of HIV comprising a substrate and an anti-ICAM-1 antibody.

30. The article of claim 29 wherein said anti-ICAM-1 antibody is impregnated in said substrate.

31. The article of claim 29 wherein said anti-ICAM-1 antibody is in coating on said substrate.

32. The article of claim 29 wherein said substrate is selected from the group consisting of sponges, condoms, intrauterine devices, cervical rings and diaphragms.

33. The article of claim 29 wherein said substrate comprises a contraceptive.

* * * * *